United States Patent [19]
Crumb et al.

[11] Patent Number: 5,984,873
[45] Date of Patent: Nov. 16, 1999

[54] INCENTIVE SPIROMETER

[75] Inventors: Douglas M. Crumb, Boonville; Rex A. Niles, Oneida; Fredrick M. Richards, Clinton; Lawrence A. Weinstein, Oneida, all of N.Y.

[73] Assignee: Diemolding Corporation, Canastota, N.Y.

[21] Appl. No.: 09/009,338

[22] Filed: Jan. 20, 1998

[51] Int. Cl.⁶ .................................................. A61B 5/08
[52] U.S. Cl. ............................................ 600/538; 482/13
[58] Field of Search ........................... 600/529, 538–541, 600/532–533; 482/13; D24/164

[56] References Cited

U.S. PATENT DOCUMENTS

| | | | |
|---|---|---|---|
| D. 319,880 | 9/1991 | Tapolcai | D24/164 |
| 436,665 | 9/1890 | Krell . | |
| 3,063,183 | 11/1962 | Long . | |
| 3,518,783 | 7/1970 | Foley . | |
| 3,555,712 | 1/1971 | Yargeau . | |
| 3,925,901 | 12/1975 | McCormick . | |
| 4,301,608 | 11/1981 | Taylor, Jr. . | |
| 4,809,706 | 3/1989 | Watson et al. | 600/538 |
| 4,897,945 | 2/1990 | Webb . | |
| 4,932,521 | 6/1990 | Au . | |
| 5,022,170 | 6/1991 | House . | |
| 5,113,612 | 5/1992 | Machen . | |
| 5,276,986 | 1/1994 | Thomas . | |
| 5,522,380 | 6/1996 | Dwork | 128/200.23 |

OTHER PUBLICATIONS

The DHD Coach 4000 Volumetric Incentive Spirometer ©1993 601–282–002A Diemolding Healthcare Division. The DHD Coach Jr. The DHD Coach 2500 The DHD Coach 4000.

*Primary Examiner*—Linda C. M. Dvorak
*Assistant Examiner*—Roy Gibson
*Attorney, Agent, or Firm*—August E. Roehrig, Jr.; Hancock & Estabrook, LLP

[57] ABSTRACT

An improved incentive spirometer adapted to introduce a flow of oxygen across the inlet for inspiratory air so that the oxygen may be drawn thereinto without requiring any change in the calibration of the device or the monitoring of the patient's usage. The device also features an integral information display receptacle in the base for storage of operational instructions. A portion of the base is transparent to that the information contained in the storage receptacle can be viewed by a patient while the device is in use, thereby permitting a patient to observe such things as the instructions for proper use of the incentive spirometer while using the device. The spirometer structure can be utilized for different patient groupings by changing a venturi plate to present a flow restricting orifice designed to accommodate the respiratory therapy and exercise needs for the particular patient grouping. Individual devices can be readily adjusted for desired results by selectively opening or closing tuning ports built into the device.

11 Claims, 6 Drawing Sheets

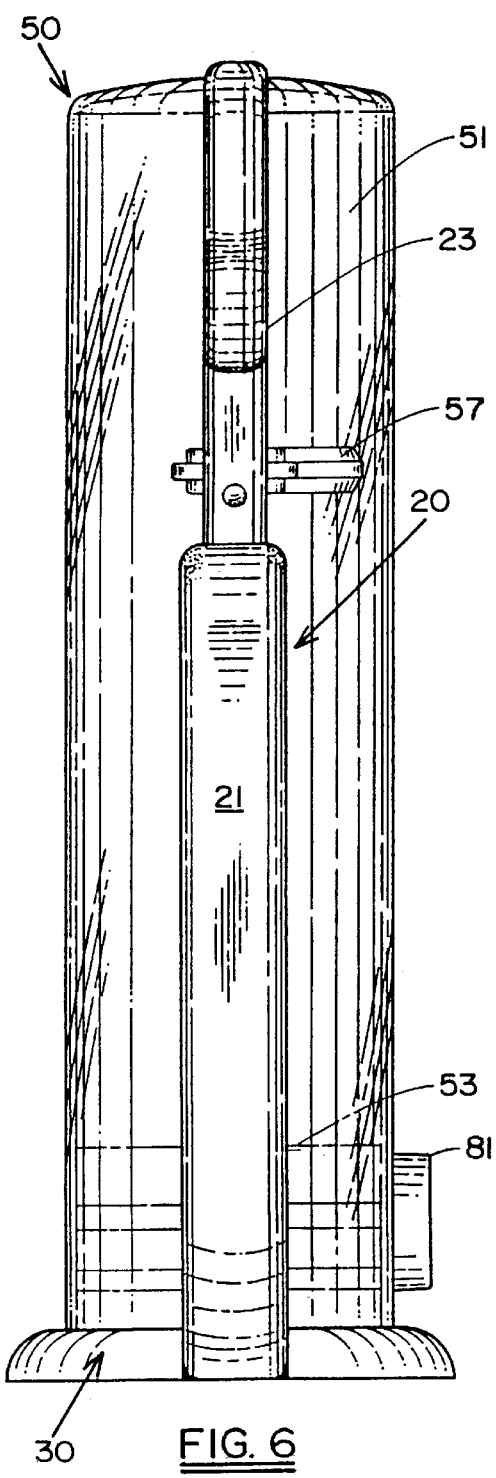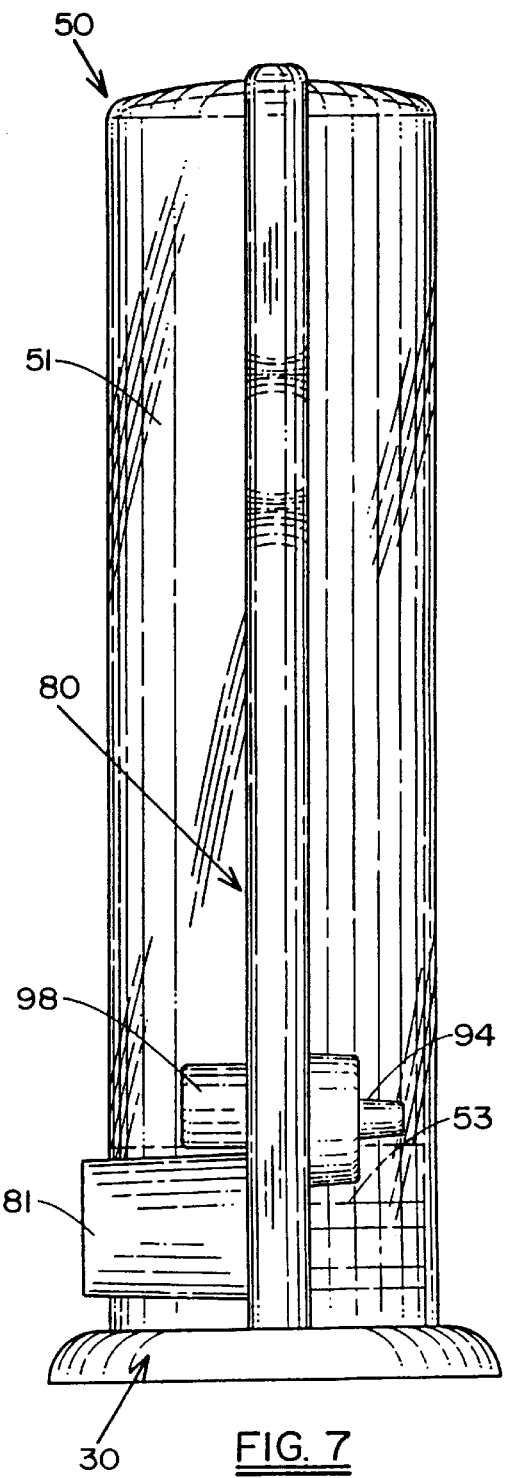

ps://5,984,873

INCENTIVE SPIROMETER

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by any one of the patent disclosure, as it appears in the Patent and Trademark Office patent files or records, but otherwise reserves all copyright and trade dress rights whatsoever.

BACKGROUND OF THE INVENTION

1. Field of the Invention

This invention relates in general to respiratory therapy devices and, in particular, to an improved incentive spirometer.

More specifically, but without restriction to the particular embodiment and/or use which is shown and described herein for purposes of illustration, this invention relates to an incentive spirometer wherein an oxygen inlet is provided to facilitate the introduction of oxygen into the device without the oxygen effecting the monitoring of a patient's use of the device, and an integral information display receptacle is provided to enable written information to be displayed while the spirometer is in use.

2. Description of Related Art

The use of incentive spirometers for respiratory care and treatment is well known, but the implementation of oxygen to supplement the use of such devices has not been utilized. Various reasons have contributed to the lack of success in the utilization of oxygen for such a purpose, primarily because of the nature of incentive spirometers, and the manner in which such devices are used in respiratory care and treatment. Incentive spirometers are utilized to monitor a patient's breathing, and to provide a controlled exercise for a patient's lungs and associated breathing apparatus. While the use of a supplemental supply of oxygen is very advantageous in the treatment of some patients when using an incentive spirometers, the introduction of oxygen into the air stream for use by the patient, can effect the patient's use of the incentive spirometer. When the oxygen is introduced into the air stream, the oxygen being supplied can drive the system because of the positive pressure added by the volume of oxygen being added. "Driving" the system in this manner effects the calibration of the incentive spirometer, and gives the patient false feedback readings by which a patient monitors their use of the devices. The present invention includes a provision for supplying oxygen to a user without interfering with the calibration of the device or the user's monitoring their use of the spirometer.

A further feature of this invention is the provision of an integral information display receptacle in the base of the incentive spirometer, which permits a patient to observe such things as the instructions for the use of the device while the device is actually in use. Providing a convenient and readily accessible place on the device itself to store instructional information, in an manner whereby the information can be referred to by a patient when using the device, allows the patient to refer to such information during therapy and exercise sessions to insure that the device is being properly used.

SUMMARY OF THE INVENTION

It is an object of this invention to improve incentive spirometers.

Another object of this invention is to provide a supply of oxygen to the inlet air of an incentive spirometer when in use by a patient without the supply of oxygen so provided interfering with the normal operation of the spirometer.

A further object of this invention is to provide a supply of oxygen to the inlet air of an incentive spirometer when in use by a patient without the source of oxygen being supplied interfering with the calibration of the spirometer.

Still another object of this invention is to provide a supply of oxygen to the inlet air of an incentive spirometer when in use by a patient without the source of oxygen so provided interfering with the patient's monitoring their use of the spirometer.

Yet another object of this invention is to provide a convenient receptacle integral with an incentive spirometer to enable written information to be stored within the device for use by a patient.

These and other objects are attained in accordance with the present invention wherein there is provided an improved incentive spirometer adapted to introduce a flow of oxygen across the inlet for inspiratory air so that the oxygen may be drawn thereinto without requiring any change in the calibration of the device or the monitoring of the patient's usage. The device also features an integral information display receptacle in the base for storage of operational instructions. A portion of the base is transparent to that the information contained in the storage receptacle can be viewed by a patient while the device is in use, thereby permitting a patient to observe such things as the instructions for proper use of the incentive spirometer while using the device. The spirometer structure can be utilized for different patient groupings by changing a venturi plate to present a flow restricting orifice designed to accommodate the respiratory therapy and exercise needs for the particular patient grouping. Individual devices can be readily adjusted for desired results by selectively opening or closing tuning ports built into the device.

DESCRIPTION OF THE DRAWINGS

Further objects of this invention, together with additional features contributing thereto and advantages accruing therefrom, will be apparent from the following description of a preferred embodiment of the present invention which is shown in the accompanying drawings with like reference numerals indicating corresponding parts throughout and which is to be read in conjunction with the following drawings, wherein:

FIG. 6 is a left side elevational view of the invention;

FIG. 7 is a right side elevational view of the invention; and

Figure 1:
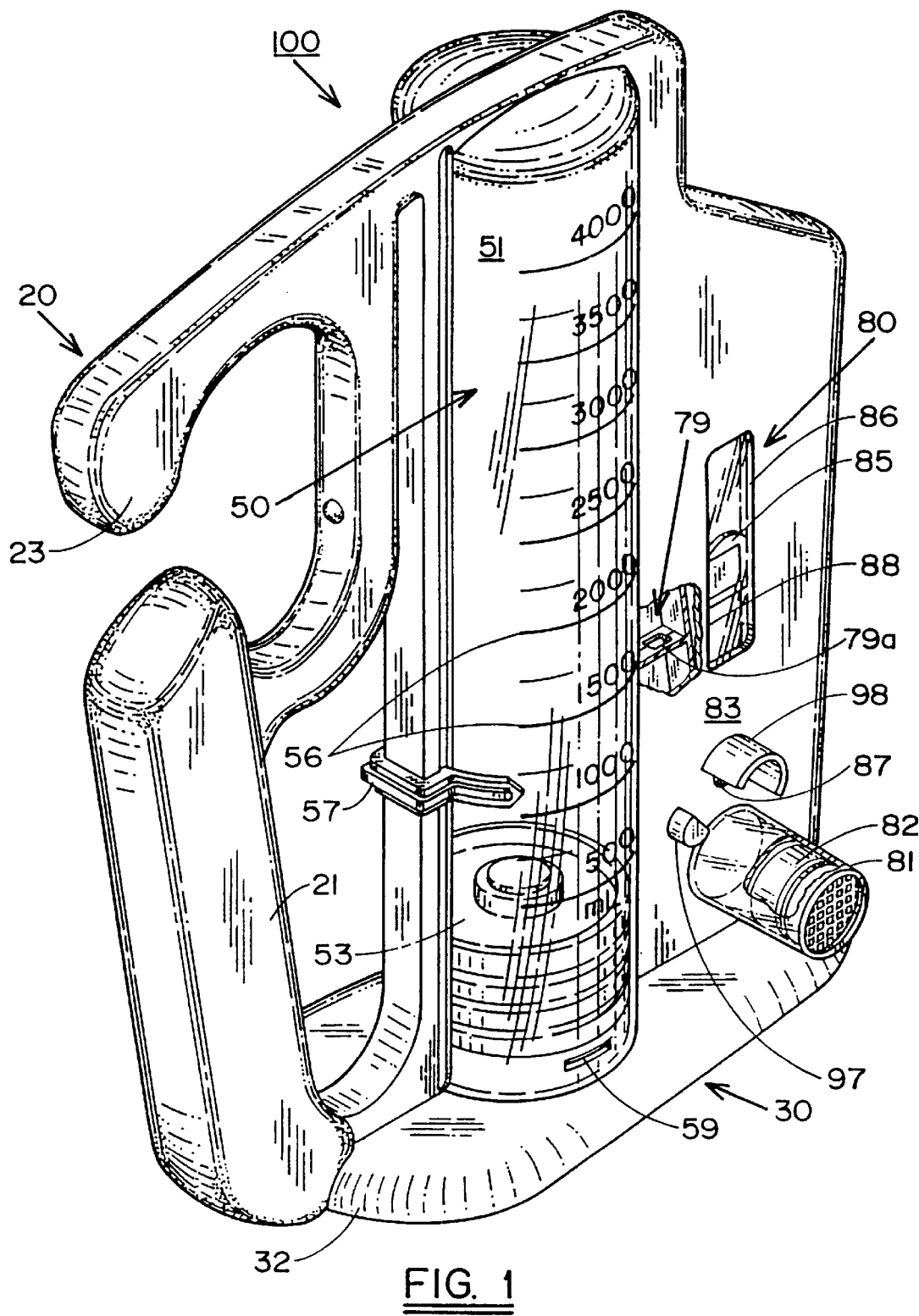
FIG. 1 is a frontal perspective view of the incentive spirometer.
Figure 2:
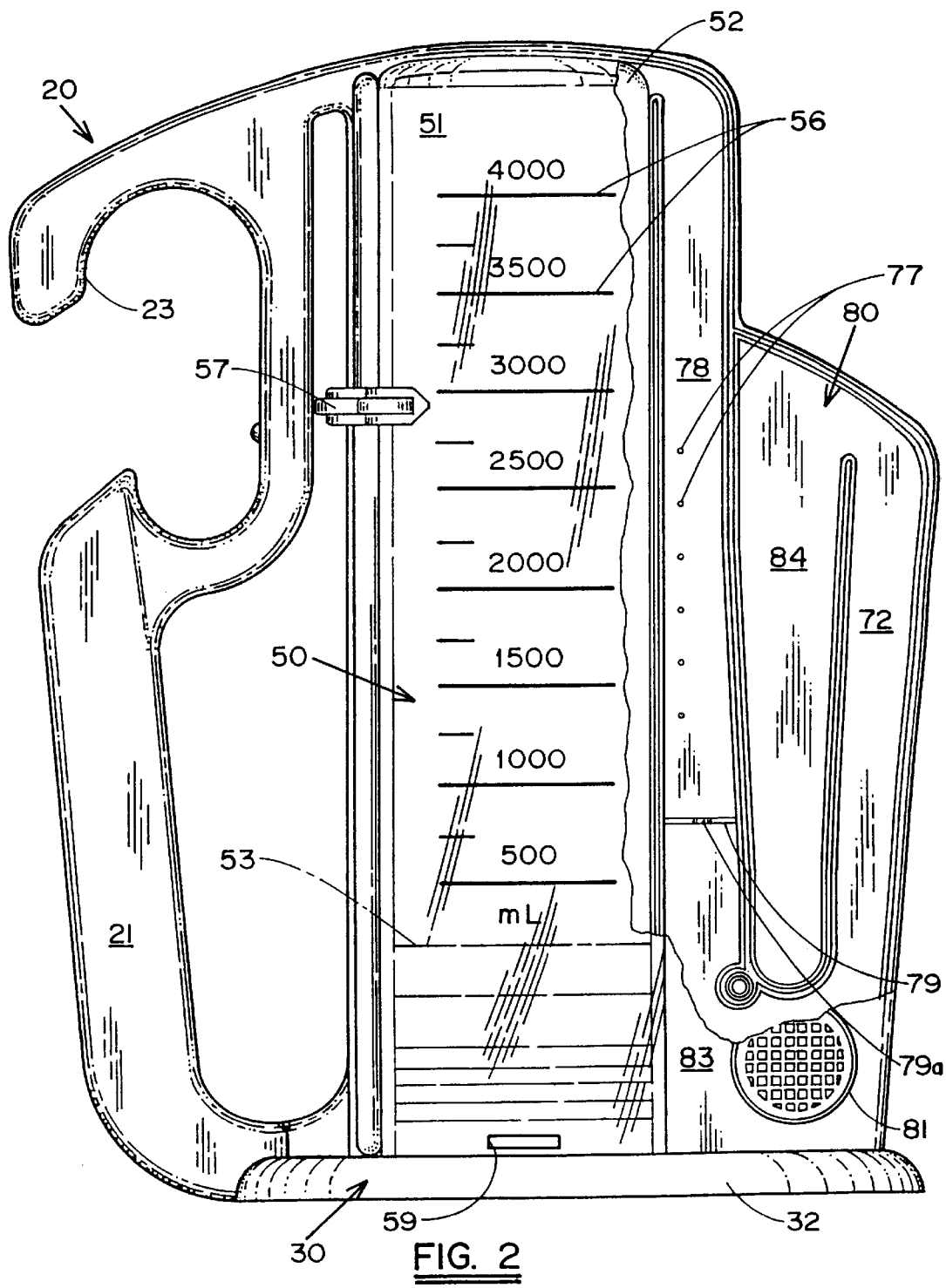
FIG. 2 is a frontal elevational view of the invention with portions broken away to better illustrate the internal construction thereof.

These and additional embodiments of the invention may now be better understood by referring to the following detailed description of the invention wherein the illustrated embodiments are described.

DETAILED DESCRIPTION OF THE INVENTION

Throughout this description, the preferred embodiment and examples shown should be considered as exemplars, rather than limitations on the apparatus and methods of the present invention.

Referring now to the drawings, there is shown an incentive spirometer 100, having a handle portion 20, a base portion 30, a volume chamber portion 50, and a monitoring portion 80. The handle portion 20 provides a convenient manner for holding and carrying the device, and for attaching the device to a bed, for example, where it can be readily accessible. The base portion 30 provides a platform upon which the device rests, and an integral information display receptacle for containing information such as the written instructions for use of the device which can be conveniently observed by a patient from the top or the bottom of the device when the device is in use. The volume chamber portion 50 provides a predetermined volume against which a patient's respiratory system is exercised for a determinable volumetric capacity to obtain the benefits of this therapy. The monitoring portion 80 provides a visual display for a patient to determine the correct flow of inspiratory air to be applied by the patient's respiratory system during therapy, and in cooperation with the volume chamber portion 50, permits the patient to determine the quantity of inspiratory air which has been drawn into the patient's lungs at the correct flow rate.

As best illustrated in FIGS. 1, 2, 3 and 8, the monitoring portion 80 includes an inlet port 81 formed as an opening in a front wall 83 of the monitoring portion through which a patient draws inspiratory air by means of a mouthpiece 91 connected to a flexible Popple tube 93. The tube 93 is sized to be securely positioned over the connecting port in which is carried a one-way valve 82 to permit a patient to draw inspiratory air through the mouthpiece 91, but which blocks the passage of expiratory air from passing back into the device. The monitoring portion 80 permits the patient to monitor the inspiratory air flow rate being applied by the patient's respiratory system during therapy, and in cooperation with the volume chamber portion 50, to monitor the volume or quantity of air being inhaled.

To this end, the monitoring portion 80 includes an indicator 85 of a predetermined weight, preferably approximately 0.5 grams, which is vertically moveable between two parallel guide rails 86 (best shown in FIG. 3) which are formed between the front wall 83 and a back wall 84 of the monitoring portion 80 defining an indicator channel 75. The channel 75 in which the indicator 85 is vertically moveable, formed between the front and back walls 83, 84 and the guide rails 86, is in fluid communication with the inspiratory air inlet port 81 so that as a patient draws inspiratory air from the mouthpiece 91, the flow of air will cause the indicator 85 to rise in the channel so formed. A pair of air channels 72 and 78 are formed in the monitoring portion 80 to provide fluid communication, respectively, between the inlet port 81 and the indicator channel 75, and the inlet port 81 and the volume chamber portion 50, for a purpose to be hereinafter described in detail. A pair of indicator stops 85a are positioned to extend across the channel 75 to define the upper and lower limits of travel of the indicator 85 within the channel.

In the preferred embodiment, a window 88 or other suitable indicia such as target or demarcation lines are formed on the front wall 83 to delineate a positional range within which a patient is to keep the indicator 85 when inhaling. In this manner, a patient can monitor the proper rate of flow of the inspiratory air which is to be drawn into the respiratory system, by keeping the indicator 85 within the target area 88 of the indicator.

On the back wall 84, a connecting oxygen inlet port 94 is formed to receive a connection from a source of oxygen. The oxygen inlet port 94 extends from the rear of the back wall 84, through the back and front walls 84 and 83 of the monitoring portion 80, and terminates at an oxygen discharge outlet 97 positioned adjacent to the inlet 81 through which a patient draws inspiratory air. The oxygen discharge outlet 97 is positioned such that the flow of oxygen is directed across an inlet 87 through which air is drawn into the device when the patient inhales through the mouthpiece 91, and not directed into the inlet 87. In this manner, the oxygen being supplied will not effect the patient created air flow applied to the device when in use. A cowling 98 partially surrounds the air inlet 87 to facilitate oxygen being drawn into the inlet 87 during use by a patient, without the flow of oxygen effecting a patient's use of the device or the monitoring of the rate of inspiratory air flow applied by a patient when using the device.

The volume chamber portion 50 includes a chamber 51 of a predetermined volume carrying a piston 53 therewithin. The air channel 78 forms a fluid connection between the inspiratory air inlet port 81 and the top 52 of the volume chamber 51. In this manner, when inspiratory air is drawn through the mouthpiece 91, the piston 53 will be drawn upwardly. If a patient is drawing inspiratory air at the desired target flow rate as shown by the indicator 85, the volume of air drawn into the patient's respiratory system can be determined by observing the calibrations 56 marked on the chamber 51. A slidable indicator 57 is carried on the chamber 51 and may be movably positioned by the patient to a preselected volume calibration mark 56 to facilitate convenient use of the device. Outlet ports 59 are formed in the bottom portion of the chamber 51 to facilitate the piston 53 returning to the bottom of the chamber 51 when the negative pressure from the patient's inspiration of air is terminated.

To adjust the time in which a desired quantity of inspiratory air has been ingested by a patient at the desired rate of flow, a venturi plate 79 is positioned across the air channel 78 to provide an orifice of a predetermined size. In this manner, a standard sized air channel 78 can be utilized in manufacturing the device, with adjustments in the calibration of the flow rate required to be applied in order to attain the target rate, being determined by the size of the orifice 79a in the venturi plate 79, and one or more tuning openings 77 which may be formed in the front wall 83.

To use the same basic spirometer construction for both adult and child patient groupings, for example, a venturi plate 79 having a different sized air-flow-restricting orifice 79a can be utilized in the air channel 78 to accommodate different volumes of air being drawn at the desired flow rate, depending upon whether the spirometer is intended to be used by children or adults. For example an orifice 79a having an opening of approximately 0.1 by 0.05 inches has been found suitable for adults, while the same spirometer structure with a venturi plate 79 having an opening of approximately 0.1 by 0.07 inches has been found suitable for children.

As best shown in FIG. 1, the venturi plate 79 comprises two portions, one portion being attached to each of the front and back walls 83 and 84, respectively, with a part of each portion being removed to form the orifice 79a. For manufacturing purposes, it has been found that one of the portions forming the venturi plate 79 is best formed with the size of the part removed to form the orifice 79a remaining constant, while the other portion forming the venturi plate 79 may be formed with the part removed varying to change the size of the orifice 79a in response to the desired volume of air to be withdrawn by the user of the device. In this manner manufacturing the dimensional changes in the opening is more easily facilitated.

After the desired size of the orifice 79a has been determined, based upon the patients with whom the spirometer is to be used, the individual spirometers are then tested for correct calibration. The tuning openings or ports 77 are all initially open, and are selectively closed for any particular spirometer in order to more precisely control the rate of flow that must be inspired by the patient in order to attain the desired volumetric goals when in use.

Figure 3:
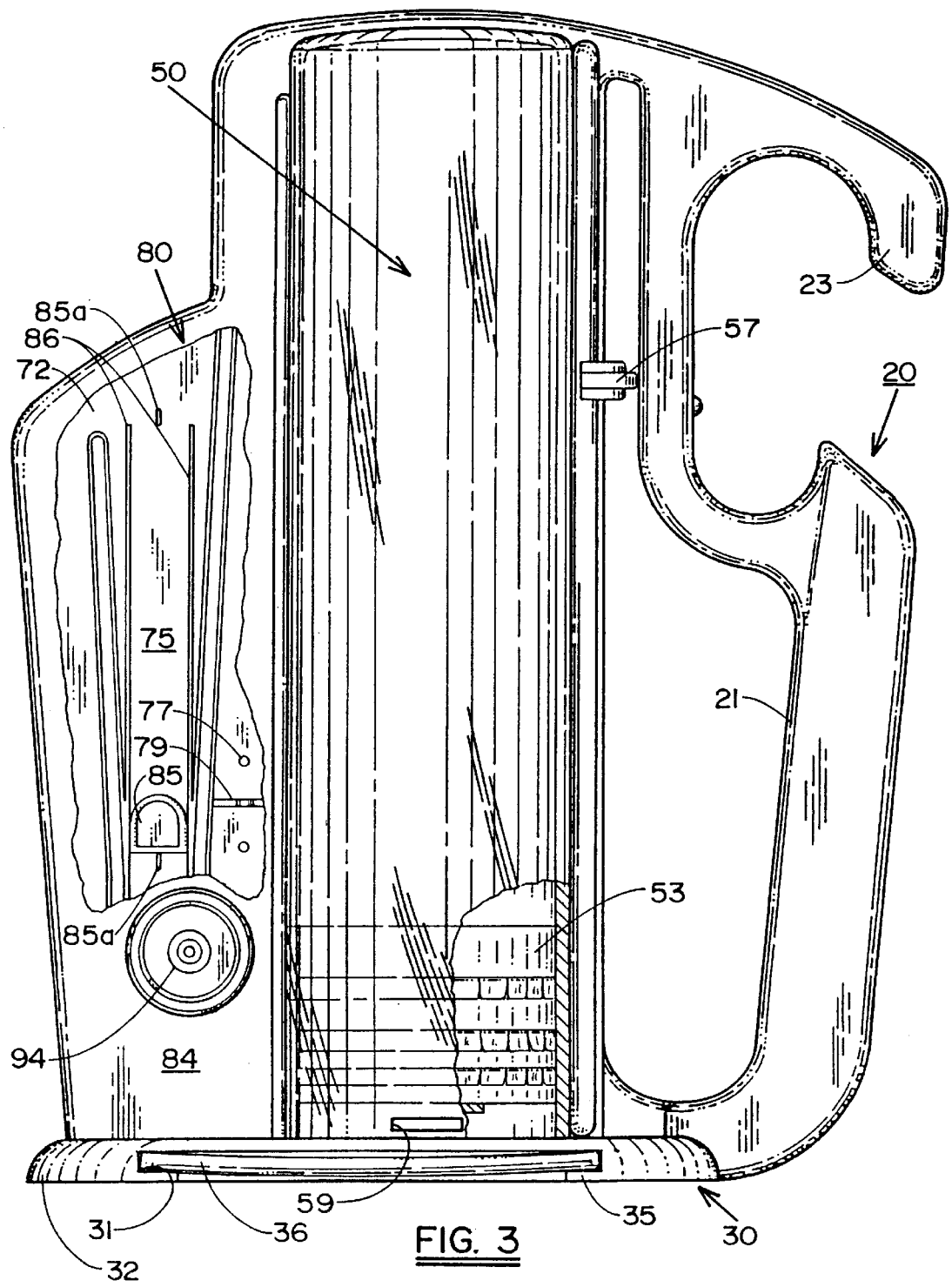
FIG. 3 is a rear elevational view of the invention with portions broken away to better illustrate the internal construction thereof.
Figure 4:
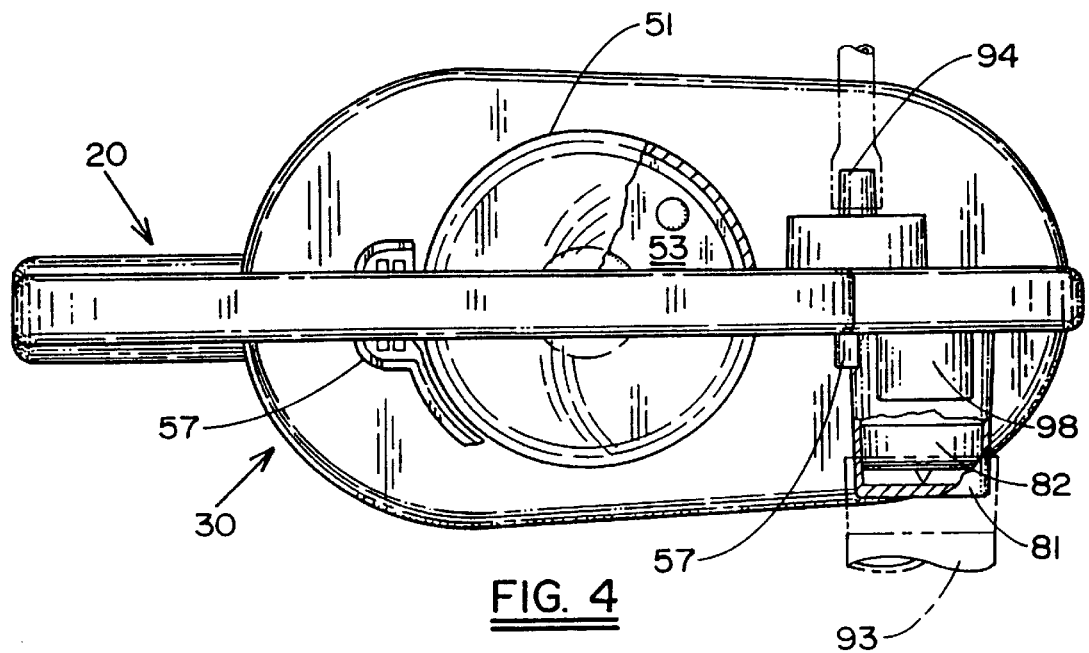
FIG. 4 is a top elevational view of the invention with portions broken away to better illustrate the internal construction thereof.
Figure 5:
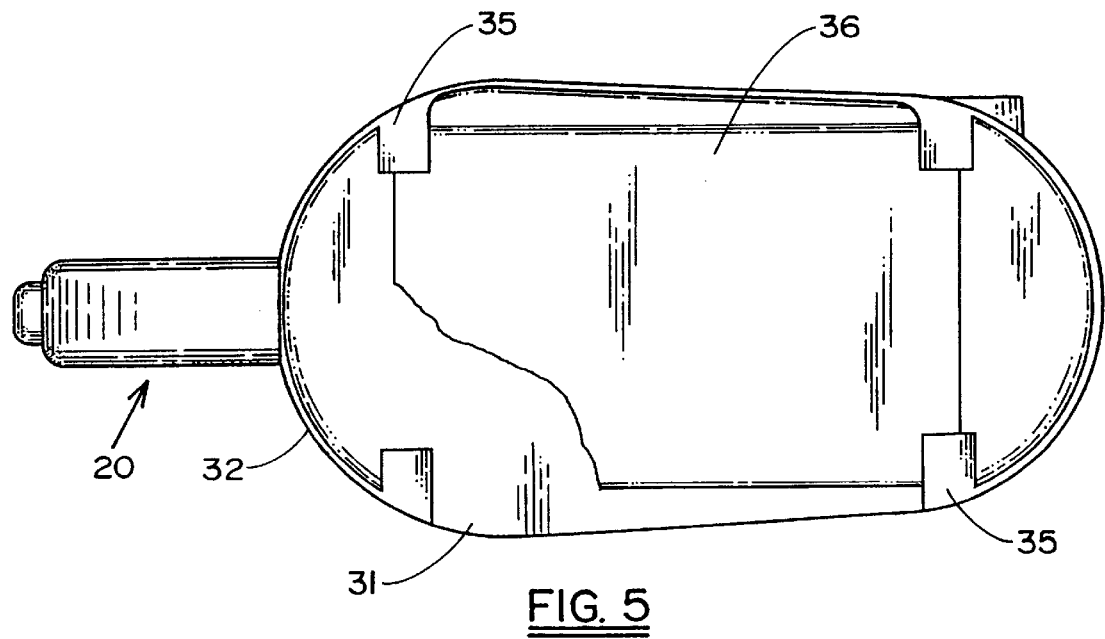
FIG. 5 is a bottom elevational view of the invention with portions broken away to better illustrate the internal construction thereof.
Figure 8:
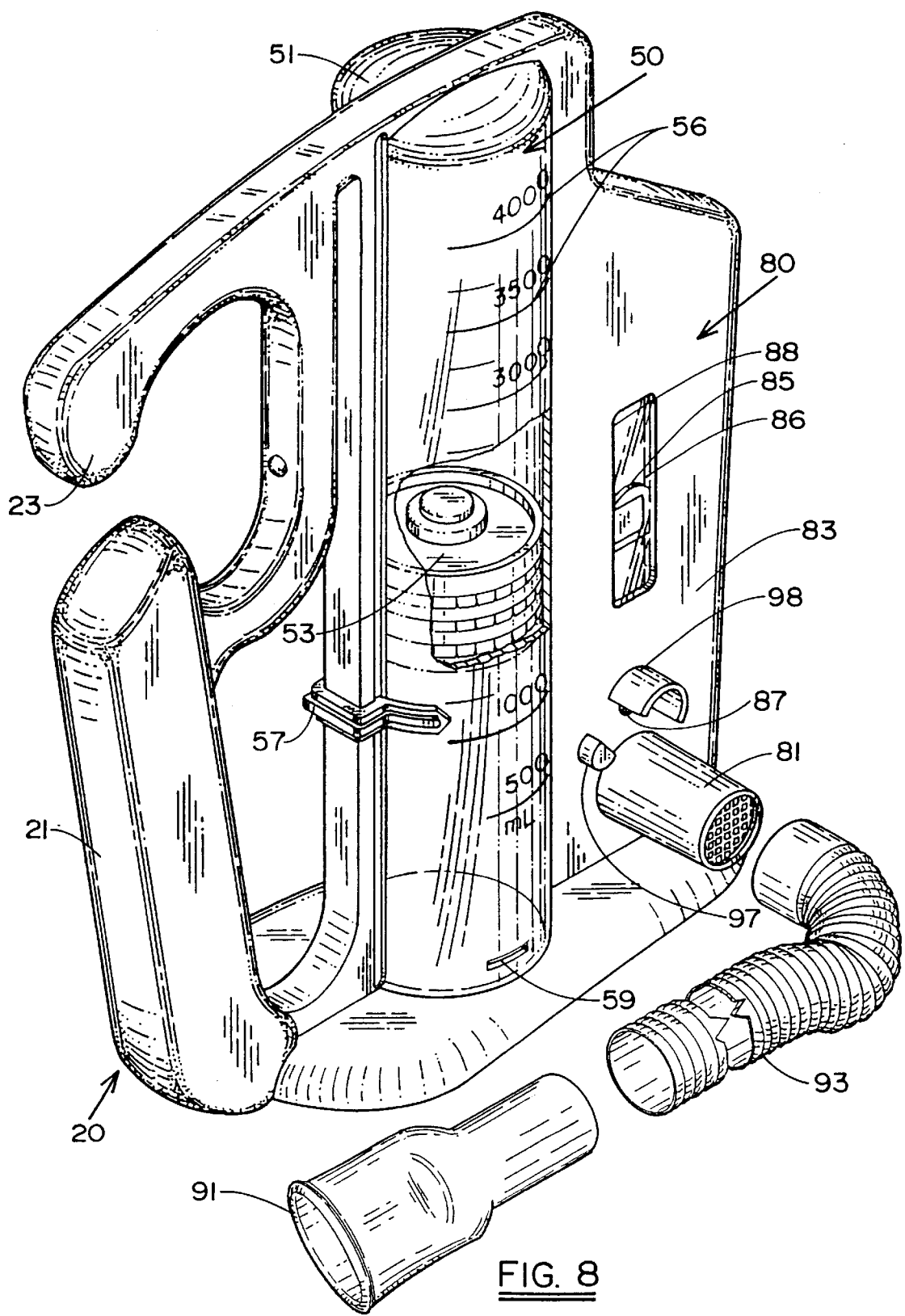
FIG. 8 is a frontal perspective view of the invention with portions broken away to better illustrate the internal construction thereof, and to illustrate a mouthpiece adapter for connecting to the incentive spirometer.

In order to permit the patient to conveniently observe the instructions for use of the device, and to maintain those instructions in an accessible fashion, the base portion 30 is formed of a transparent material with an opening 31 in a skirt portion 32 of the base, best illustrated in FIGS. 3 and 5. The opening 31 is formed between the top of the base and base pads 35 upon which the device stands. In this manner documentary materials, such as the instructions 36 for the use of the device, can be inserted into the base through the opening 31, and will be supported by the base pads 35 above the surface upon which the device is placed. Because the base is preferably formed of a transparent material, the instructions may be folded in a manner so that they are observable through the top and the bottom of the base to facilitate a patient's reference to them while the device is in use.

The handle portion 20 is joined at its lowermost end to the base portion 30, and at its uppermost end to the volume chamber portion 50. A closed portion is formed between a handle 21 and the chamber 51 enabling a patient to grasp and carry the device. An open hook projection 23 is formed by the uppermost part of the handle 21 enabling the device to be conveniently hung over a rail or a portion of a bed for convenient access by patients that are so confined.

While this invention has been described in the specification and illustrated in the drawings with reference to preferred embodiments, the structures of which have been disclosed herein, it will be understood by those skilled in the art to which this invention pertains that various changes may be made, and equivalents may be substituted for elements of the invention without departing from the scope of the claims. Therefore, it is intended that the invention not be limited to the particular embodiment disclosed in the specification and shown in the drawings as the best mode presently known by the inventors for carrying out this invention, nor confined to the details set forth, but that the invention will include all embodiments, modifications and changes as may come within the scope of the following claims:

It is claimed:

1. In an incentive spirometer wherein a patient induced source of inspiratory air is applied to a volumetric capacity indicating chamber and an inspiratory air flow rate monitoring chamber to permit a patient to self-administer respiratory therapy by inhaling a predetermined volume of air at a desired inhalation rate, the improvement comprising means for applying oxygen to the source of inspiratory air inspired by a patient without effecting the inhalation rate or volumetric capacity of the patient induced source of inspiratory air as monitored or determined by the incentive spirometer.

2. In an incentive spirometer having a support base and wherein a patient induced source of inspiratory air is applied to a volumetric capacity indicating chamber and an inspiratory air flow rate monitoring chamber to permit a patient to self-administer respiratory therapy by inhaling a predetermined volume of air at a desired inhalation rate, the improvement comprising said support base having a portion thereof which is transparent, and a slot formed integral with a portion of said support base and adjacent to said transparent portion for receiving therethrough display information visually observable to a patient through said transparent portion when self-administering respiratory therapy, and a plurality of supports spaced from said slot to support the display information placed therethrough.

3. In an incentive spirometer having a support base and wherein a patient induced source of inspiratory air is applied to a volumetric capacity indicating chamber and an inspiratory air flow rate monitoring chamber to permit a patient to self-administer respiratory therapy by inhaling a predetermined volume of air at a desired inhalation rate, the improvement comprising said support base having a portion thereof which is transparent, and means integral with said support base and adjacent to said transparent portion for receiving display information visually observable to a patient through said transparent portion when self-administering respiratory therapy said improvement further including means for applying oxygen to the source of inspiratory air inspired by a patient without effecting the inhalation rate or volumetric capacity of the patient induced source of inspiratory air as monitored or determined by the incentive spirometer.

4. The incentive spirometer of claim 1 wherein said means for applying oxygen to the source of inspiratory air inspired by a patient without effecting the inhalation rate or volumetric capacity of the patient induced source of inspiratory air as monitored or determined by the incentive spirometer comprises a source of oxygen positioned to direct a flow of oxygen adjacent to and across an inspiratory air inlet without directing the oxygen flow into the inspiratory air inlet.

5. The incentive spirometer of claim 4 wherein said means for applying oxygen to the source of inspiratory air inspired by a patient without effecting the inhalation rate or volumetric capacity of the patient induced source of inspiratory air as monitored or determined by the incentive spirometer further includes a cowling partially surrounding said inspiratory air inlet and having an opening therein facing toward said source of oxygen for receiving said oxygen therein without applying any oxygen flow from the oxygen source directly into said incentive spirometer.

6. In an incentive spirometer having a support base and wherein a patient induced source of inspiratory air is applied to a volumetric capacity indicating chamber and an inspiratory air flow rate monitoring chamber to permit a patient to self-administer respiratory therapy by inhaling a predetermined volume of air at a desired inhalation rate, the improvement comprising means extending between said support base and said volumetric capacity indicating chamber forming a closed-loop handle for carrying said incentive spirometer and an open hook by which said incentive spirometer may be hung.

7. In an incentive spirometer wherein a patient induced source of inspiratory air is applied to a volumetric capacity indicating chamber and an inspiratory air flow rate monitoring chamber to permit a patient to self-administer respiratory therapy by inhaling a predetermined volume of air at a desired inhalation rate, the improvement comprising means for mutually exclusively selectively controlling the patient induced inspiratory air inhalation rate applied to said volumetric capacity indicating chamber and said inspiratory flow rate monitoring chamber.

8. The incentive spirometer of claim 7 wherein said means for mutually exclusively selectively controlling the patient induced inspiratory air inhalation rate applied to said volumetric capacity indicating chamber and said inspiratory flow rate monitoring chamber comprises a venturi plate positioned in a path of inspiratory air flow to said volumetric capacity indicating chamber.

9. The incentive spirometer of claim 8 wherein said means for mutually exclusively selectively controlling the patient induced inspiratory air inhalation rate applied to said volumetric capacity indicating chamber and said inspiratory flow rate monitoring chamber further includes a plurality of tuning ports in said path of inspiratory air flow to said volumetric capacity indicating chamber selectively opened or closed to control the patient induced inspiratory air inhalation rate.

10. The incentive spirometer of claim 8 wherein said venturi plate is formed in two portions with a part of each portion being removed to define an orifice therethrough.

11. The incentive spirometer of claim 10 wherein one of said venturi plate portions has a part removed to define said orifice which is greater than the part removed from the other of said venturi plate portion.

* * * * *